(12) United States Patent
Liu et al.

(10) Patent No.: US 12,195,638 B2
(45) Date of Patent: Jan. 14, 2025

(54) COMPOSITIONS AND METHODS OF MAKING A THIN FILM AND APPLICATIONS THEREOF

(71) Applicant: ALEO BME, INC., State College, PA (US)

(72) Inventors: Chao Liu, State College, PA (US); John J Round, State College, PA (US)

(73) Assignee: ALEO BME, INC., State College, PA (US)

( * ) Notice: Subject to any disclaimer, the term of this patent is extended or adjusted under 35 U.S.C. 154(b) by 1066 days.

(21) Appl. No.: 17/040,253

(22) PCT Filed: Mar. 14, 2019

(86) PCT No.: PCT/US2019/022257
§ 371 (c)(1),
(2) Date: Sep. 22, 2020

(87) PCT Pub. No.: WO2019/182862
PCT Pub. Date: Sep. 26, 2019

(65) Prior Publication Data
US 2021/0363381 A1    Nov. 25, 2021

Related U.S. Application Data

(60) Provisional application No. 62/646,585, filed on Mar. 22, 2018.

(51) Int. Cl.
*C09D 175/06* (2006.01)
*A61L 26/00* (2006.01)
(Continued)

(52) U.S. Cl.
CPC ........ *C09D 175/06* (2013.01); *A61L 26/0019* (2013.01); *A61L 26/0066* (2013.01);
(Continued)

(58) Field of Classification Search
None
See application file for complete search history.

(56) References Cited

U.S. PATENT DOCUMENTS 4,156,067 A    5/1979  Gould
4,929,667 A    5/1990  Ban et al.
(Continued)

OTHER PUBLICATIONS

Oprea, Effect of Solvent Interactions on the Properties of Polyurethane Films, High Performance Polymers, 17: pp. 163-173. (Year: 2005).*

(Continued)

*Primary Examiner* — Lakshmi S Channavajjala
(74) *Attorney, Agent, or Firm* — Maynard Nexsen PC; Candice Cashman; John P. Zimmer

(57) ABSTRACT

In some embodiments, a film forming composition described herein comprises an aliphatic polyisocyanate; an aliphatic polyfunctional nucleophile; a chain extender; a first solvent; and a second solvent, wherein an evaporation rate of the first solvent and an evaporation rate of the second solvent are within 150% of each other, the percentage being based on the larger value. In some embodiments, a method of forming a film on a substrate is described herein, the method comprising combining a polyisocyanate with a polyol to form a polyurethane pre-polymer; combining the polyurethane pre-polymer with a chain extender to form a polymer; and applying the polymer to the substrate.

25 Claims, 6 Drawing Sheets

(51) Int. Cl.
    *C08G 18/10*     (2006.01)
    *C08G 18/40*     (2006.01)
    *C08G 18/42*     (2006.01)
    *C08G 18/48*     (2006.01)
    *C08G 18/75*     (2006.01)

(52) U.S. Cl.
    CPC ......... *C08G 18/10* (2013.01); *C08G 18/4018* (2013.01); *C08G 18/4277* (2013.01); *C08G 18/4833* (2013.01); *C08G 18/755* (2013.01)

(56) References Cited

U.S. PATENT DOCUMENTS

| | | |
|---|---|---|
| 6,433,073 B1 | 8/2002 | Kantner et al. |
| 2013/0101540 A1 | 4/2013 | Unal et al. |
| 2015/0246994 A1 | 9/2015 | Moore et al. |

OTHER PUBLICATIONS

Solvent Effects in Polyurethane Cure: a Model Study. American Chemical Society, p. 3928-3938 (Year: 2012).*

Agrawal, et al. "The Efficacy of Aceton in the Sterilisation of Ophthalmic Instruments,", Indian Journal of Ophthalmology, 1993, vol. 41, p. 20-22, p. 1, Abstract.

PCT International Search Report for PCT/US2019/022256, Jun. 7, 2019.

International Bureau, International Preliminary Report on Patentability based on PCT/US2019/022257, Oct. 1, 2020.

\* cited by examiner

COMPOSITIONS AND METHODS OF MAKING A THIN FILM AND APPLICATIONS THEREOF

CROSS-REFERENCE TO RELATED APPLICATIONS

This application is a U. S. National Phase of PCT/US2019/22257, filed Mar. 14, 2019 which claims priority under 35 U.S.C. § 119 to U.S. Provisional Patent Appl. No. 62/646,585, filed Mar. 22, 2018, the entirety of which is incorporated by reference herein.

FIELD OF INVENTION

The invention is generally related to polymeric thin films, and more specifically, to peelable polymeric thin films.

BACKGROUND

Thin films and film compositions are used in a variety of industries. For example, various thin films have been used in the healthcare industry as a protective barrier for exposed surfaces, such as a dermis layer of human or animal skin, or on devices having delicate mechanics. For applications in the healthcare industry, ideal thin films for covering the skin will conform to the complex contours of the skin, remain adhered for extended periods of time, exhibit tensile and strain properties similar to the natural dermis layer, facilitate transpiration, and be non-toxic. Various thin film dressings have been employed, each with attempting to fill all of the ideals for thin films. However, these conventional thin films present many disadvantages. For example, many of the conventional thin films use an adhesive-coated thin polymer film on a removable liner. The polymer film is removed from the liner, and the adhesive-coated surface is applied to a person's skin. However, the polymer film tends to crease and stick to itself, and become unusable during the application process. While increasing the thickness of the polymer film can sometimes relieve some of these problems, the increased thickness often results in the polymer film being unable to conform to the contours of the skin, failing to feel like natural skin, and having reduced transpiration. Additionally, because the conventional polymer films are prefabricated and applied to a liner, the polymers films have to be fabricated into a variety of different dimensions to accommodate different sized applications and locations.

Thus a need exists for a thin polymer film having improved properties.

SUMMARY

In one aspect, thin film and thin film compositions are described herein which, in some embodiments, can offer one or more advantages over prior thin films and thin film compositions. In some embodiments, for example, the thin films described herein can exhibit desirable elastic, peelable, and/or durable physical properties. The thin film can have applications in a number of different fields, including human health care, industrial equipment, veterinary care, cosmetics, art, cinema, and athletics industries.

In some embodiments, a film forming composition is described herein comprising an aliphatic polyisocyanate; an aliphatic polyfunctional nucleophile; a chain extender; and a solvent. In some embodiments, a composition is described herein comprising a thin film, the thin film comprising a polymer formed from a reaction product of an aliphatic polyisocyanate; an aliphatic polyfunctional nucleophile; and a chain extender. In some cases, a ratio of isocyanate groups of the polyisocyanate to a total of hydroxyl and amino groups of the polyfunctional nucleophile and chain extender is 1.5:1 to 1:1.

In some instances, a polyisocyanate and a polyfunctional nucleophile can be combinable to form a pre-polymer. A chain extender described herein can be combinable with the pre-polymer to form a polymer.

In some instances, a solvent described herein comprises a first solvent and a second solvent. An evaporation rate of the first solvent and an evaporation rate of the second solvent are within 150% of each other, the percentage being based on the larger value; and/or in some cases within 50 to 1500% of an evaporation rate of n-butyl acetate. In some cases, a mixture of the first solvent and the second solvent can have a polarity index of 1 to 7, and/or a dielectric constant of 2 to 30. Furthermore, in some cases, a mixture of the first solvent and the second solvent has a total vapor pressure of 4 to 70 mmHg according to Raoult's law.

In some embodiments, a solvent, such as a first solvent and a second solvent described herein, can comprise water, acetone, ethanol, methyl ethyl ketone, ethanol, isopropanol, methyl acetate, ethyl acetate, butyl acetate, methyl propyl acetate, methyl isobutylketone, tetrahydrofuran, N-methylcyclohexanone, a siloxane, a linear alkane, a branched alkane, a cyclic alkane, or any combination thereof. In some instances, the first solvent is different from the second solvent.

A polyisocyanate described herein can comprise hexamethylene diisocyanate (HDI), isophorone diisocyanate (IPDI), bis(4-isocyanatocyclohexyl) methane, butane diisocyanate (BDI), a lysine diisocyanate, lysine triisocyanate, tris(6-isocyanatohexyl) isocyanurate or any combination thereof.

A polyfunctional nucleophile described herein can comprise a polyol, a polyamine, a mercaptan, or any combination thereof.

In some embodiments, a chain extender described herein is an aliphatic, a siloxane, or an ether. In some cases, the aliphatic, siloxane, and ether are a polyamine, a polyol, or any combination thereof. The aliphatic polyamine can comprise ethylene diamine, butylene diamine, pentylene diamine, hexamethylenediamine, isophorondiamine, a piperazine, or any combination thereof.

In some instances, a thin film described herein has an average thickness of 20 to 250 microns.

In some embodiments, a solvent described herein can be an antimicrobial solvent. For example, in some cases, the antimicrobial solvent can comprise ethanol, propanol, isopropanol, butanol, isobutanol, or any combination thereof.

In some instances, a thin film or composition described herein can comprise an additive, the additive comprising an antimicrobial agent, a growth factor, a peptide, a therapeutic agent, a biological regenerative agent, a cosmetic agent, a metal anti-oxidant, or any combination thereof.

In another aspect, methods of forming a thin film on a substrate are described herein, which, in some embodiments, can offer one or more advantages over other methods of forming a thin film on a substrate. For example, in some embodiments, methods of forming the film described herein are simple, efficient, scalable, inexpensive, reproducible, compatible with biological tissue, and/or has desirable physical properties.

In some embodiments, a method of forming a film on a substrate comprises applying a polyisocyanate, a polyfunctional nucleophile, and a chain extender to the substrate. In some cases, the polyisocyanate and the polyfunctional nucleophile are first combined to form a pre-polymer, and the chain extender is subsequently combined with the formed pre-polymer to prepare a film-forming polymer, and this film-forming polymer is applied to the substrate.

In some embodiments, a method of forming a film on a substrate comprises combining a polyisocyanate with a polyol to form a polyurethane pre-polymer; combining the polyurethane pre-polymer with a chain extender to form a polymer; and applying the polymer to the substrate.

In some instances, a pre-polymer and/or a polymer described herein are formed in a first solvent and a second solvent mixture, wherein the first solvent is different from the second solvent. For example, in some cases the first solvent and the second solvent mixture can comprise the pre-polymer and/or the polymer.

In some instances, a solvent, such as a first solvent and a second solvent, comprises water, acetone, ethanol, methyl ethyl ketone, propanol, isopropanol, butanol, isobutanol, methyl acetate, ethyl acetate, butyl acetate, methyl propyl acetate, methyl isobutylketone, tetrahydrofuran, N-methylcyclohexanone, a siloxane, a linear alkane, a branched alkane, a cyclic alkane, or any combination thereof.

In some cases, an evaporation rate of the first solvent and an evaporation rate of the second solvent are within 150% of each other, the percentage being based on the larger value; or within 50 to 1500% of the evaporation rate of n-butyl acetate. In some cases, a mixture of the first solvent and the second solvent has a polarity index of 1 to 7 or a dielectric constant of 2 to 30. Moreover, in some cases, a mixture of the first solvent and the second solvent has a total vapor pressure of 4 to 70 mmHg according to Raoult's law.

In some embodiments, methods described herein further comprise applying a solvent or solvent mixture to the substrate. The solvent or solvent mixture can in some instances be an antimicrobial solvent that sterilizes a surface of the substrate.

In some embodiments, a polyisocyanate described in methods herein is an aliphatic polyisocyanate. For instance, the polyisocyanate can comprise hexamethylene diisocyanate (HDI), isophorone diisocyanate (IPDI), bis(4-isocyanatocyclohexyl) methane, butane diisocyanate (BDI), a lysine diisocyanate, lysine triisocyanate, tris(6-isocyanatohexyl) isocyanurate or any combination thereof.

A polyfunctional nucleophile in some cases is an aliphatic and comprises a polyol, a polyamine, a mercaptan, or any combination thereof.

A chain extender in some cases comprises an aliphatic polyamine including ethylene diamine, butylene diamine, pentylene diamine, hexamethylenediamine, isophorondiamine, piperizine, or any combination thereof; an ether including an amine terminated polypropylene glycol, an amine terminated polyethylene glycol, or a combination thereof; or a combination of the aliphatic polyamine and the ether.

In some embodiments, methods described herein can further comprise applying an additive to the substrate, the additive comprising a antimicrobial agent, a growth factor, a peptide, a therapeutic agent, a biological regenerative agent, a cosmetic agent, a dye, a metal anti-oxidant, or any combination thereof.

In another aspect, a method of coating a surface of biological tissue comprises applying a composition described herein to the surface of the biological tissue.

These and other embodiments are described in greater detail in the detailed description and examples which follow.

DETAILED DESCRIPTION

Figure 1:
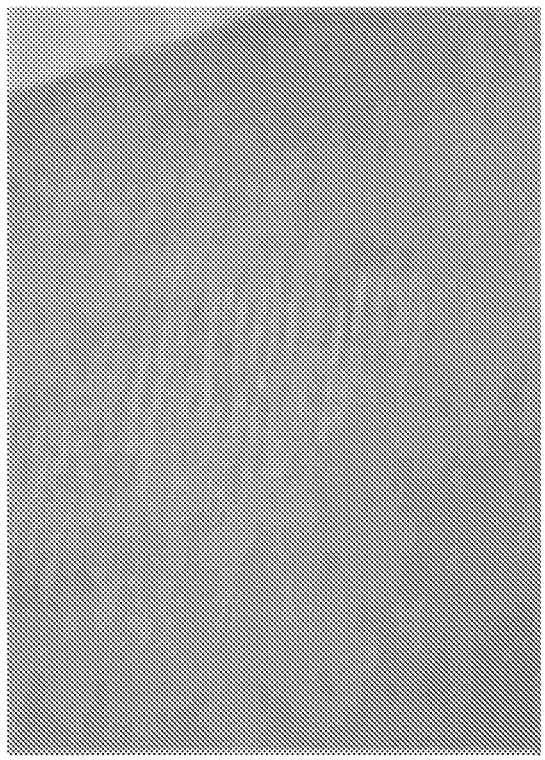
FIG. 1 is a photo of an exemplary thin film applied to human skin.

Embodiments described herein can be understood more readily by reference to the following detailed description, drawings, and examples and their previous and following descriptions. Elements, apparatus, and methods described herein, however, are not limited to the specific embodiments presented in the detailed description, drawings, and examples. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

All molecular weights described herein are weight average molecular weights unless expressly described otherwise.

The terms "thin film," "polymeric film," "polymeric thin film," and "film" are used interchangeably throughout this disclosure, and should be interpreted as having the same meaning unless expressly stated otherwise.

Thin film coatings serve a number of purposes for a broad range of applications, including across electronics, display, semiconductor, medical implants and surgical tools, human/animal tissues and many others. In biomedical field, biocompatible thin film coatings are used to protect devices and tissues from contamination such as bacterial and dust, offer a physical barrier and protection, prevent water loss and promote wound healing and so on.

Depending on applications, thin film coatings are expected to improve aesthetic appearance and wear resistance, reduce galling between sliding components, and increase lubricity. Functional coatings are often considered to confer bacterial barrier, antimicrobial, antifouling to the coated devices and biological tissues.

Thin film coating on human skin is particularly challenging. Human skin is a living and complex material, composed three layers which are epidermis, dermis, and stratum corneum. The epidermis layer is composed of partially keratinized cells that are progressively dehydrated during their migration to the outer surface, where they form the stratum corneum (SC) layer. The SC comprised of a thin bi-phasic layer of 10-20 cells with an average thickness between 25-200 nm depending on the body site. The SC is commonly described as a "brick and mortar" structure because it is composed of "brick" regions, the corneocytes, surrounded by a "mortar" phase of fatty acids, ceramides, cholesterol and water. The surface of the SC is coated with Skin Surface Lipid Film (SSLF), a mixture of sebum from the sebaceous glands and lipids secreted by keranocytes. It is well known that the SC layer plays important role in the hydration and adhesion properties of the skin. However, the SC layer has been considered a dead but highly dynamic structure, whereas the SSLF is constantly refreshing and the liquid molecules in SSLF are in fast reorientation mode. The complex composition and dynamic nature of SC and SSLF layers and the soft and elastic nature of the skin, and the constant stretching and recovering motion of skin during body movements places significant challenges for identifying ideal film forming solutions for skin coating applications.

The current skin coating materials or products are often liquid formulations that can be painted or sprayed on the skin to form a thin film coating. For example, NewSkin® is an organic solvent-based solution composed of nitrocellulose and ethanol/acetate/acetone solvents. While New Skin® forms a thin film, the nitrocellulose component results in a stiff film that is not compliant with the soft and elastic skin tissues, which can cause uncomfortable sensations to the users. Additionally, aesthetically undesirable crack lines are commonly observed on the nitrocellulose film a few hours after application on the skin and also make it hard to be peeled as an intact film. Moreover, the New Skin® film has a limited lifetime, displaying edging within 24 hours following application.

KeriCure® is a water-based polyacrylate emulsion solution in the market for skin application. While it displays elastic properties, KeriCure® is extremely weak in tensile strengths compared to skin. Moreover, KeriCure® film does not provide a true sensation of protection due to its weak mechanical properties, and users often need repeated applications on the skin to achieve sufficient coverage. The KeriCure® solution itself also has very low viscosity, and commonly "runs away" from the desired location of skin during applications. Example 15 described herein shows "run away" of KeriCure® on human skin.

NexCare® is another solvent-based liquid formulation composed of acrylate terpolymer and polyphenylmethylsiloxane as film forming polymer components, and hexamethyldisiloxane as a solvent component Similar to KeriCure®, NexCare® also has weak tensile properties, and fails to provide a true sensation of protection, leaving a wound under film still sensitive to physical frication or contact. Consequently, NexCare® films are too thin and mechanically inferior to natural skin, thus unable to provide a protection sensation and a barrier for germs and dusts. Moreover, it is very hard to peel off from skin in part due to its weak mechanical properties and extremely thin film nature. The NexCare® solution itself is also hard to stick on skin, often requiring multiple applications. Particularly, the NexCare® solution has a very low viscosity, and "runs away" from an application site on the skin and sticks to other locations, ultimately creating an off-site mess.

Consequently, while many skin-mimicking thin films have been proposed, each of these thin films have been unable to mimic and adapt to the complexity of the skin outer structures and dynamic compositions.

Thus, in contrast to current thin films, an ideal thin film forming solution is one that can be easily applied on the skin without run-away and can quickly form a thin film. An ideal thin film can, in some cases, have sufficient skin adhesion strength to adhere on skin at least 2-3 days without edging up, while still retaining the ability to be peeled as an intact film like a regular bandage for easy removal when needed. To prevent dust or microbe penetration before it is peeled off, it is highly desirable to main the intactness of the film. In some cases, an ideal thin film can provide a good sensation of protection like a regular bandage, but be transparent without crack formation for aesthetic purposes. Additionally, an ideal thin film will be biocompatible without a toxicity concern in many cases. In some instances, an ideal thin film will be mechanically compliant to natural skin and breathable to facilitate quick wound healing.

Traditionally, solvent systems used in polyurethane and/or poly(urethane-urea)-based thin films have been tailored to address the solubility of thin film polymeric components. However, as described herein, the mechanical properties of an ideal thin film have unexpectedly been found to be very dependent on not only the particular combination of polymeric components, but also the solvents being used. Specifically, it has been found that the physical properties of thin films having the same or similar polymer components can vary dramatically depending on what solvent system is used, and that solubility is not the only factor to be considered when choosing a solvent system. For example, as described herein in more detail, the physical properties of the same or similar polyurethane and/or poly (urethane-urea)-based thin films will be different when different solvent systems are used with the same polymeric components. As described herein, by selecting solvent systems having a particular evaporation rate, dielectric constant, vapor pressure, and/or polarity index, the mechanical properties including adhesion properties of the resulting thin films can be controlled. It has been discovered that particular solvent systems not only control appropriate solvent evaporation rates, film formation rates, and viscosities of thin film forming solutions to avoid quick run-away from skin, but also control film morphologies, such as the final mechanical properties, aesthetic appearance (such as transparency and crack formation), and/or surface finishing of the resulting thin film.

Consequently, disclosed herein are particular thin film-forming compositions using combinations of polymers and solvent systems that display unexpected and surprisingly superior thin film mechanical properties compared to other thin films having similar polymeric components, but different solvent systems.

I. Film Composition

Thin film and thin film compositions are described herein which, in some embodiments, can offer one or more advantages over prior thin films and thin film compositions. In some embodiments, for example, thin films described herein can be formed in situ on a surface, and exhibit desirable elastic, peelable, and/or durable physical properties, such as being applicable to skin without "run-away", and being quickly formed upon application. In some instances, thin film compositions described herein can be applied to skin as a liquid bandage that cures to form a thin film over the skin. In some instances, thin films described herein have sufficient skin adhesion strength to adhere on skin at least 2-3 days without edging up, while still retaining the ability to be peeled as an intact film like a regular bandage for easy removal when needed. Furthermore, in some instances, thin films described herein can provide a good sensation of protection like a regular bandage, but be transparent without crack formation. Moreover, thin films described herein can exhibit desirable biocompatible properties such as being non-cytotoxic, implantation compatible, non-pyrogenic, non-irritant, non-sensitizing, forming a microbial barrier, and/or low systemic toxicity. In some embodiments, the thin films described herein exhibit desirable metal anti-oxidation and material coating properties.

In some embodiments a film forming composition comprises a polyisocyanate; a polyfunctional nucleophile; a chain extender; and a solvent. In some embodiments, a composition comprises a thin film comprising a polymer formed from a reaction product of a polyisocyanate; a polyfunctional nucleophile; and a chain extender. The polyisocyanate and the polyfunctional nucleophile can be combinable to form a pre-polymer, and the chain extender is combinable with the pre-polymer to form the thin film. The ratio of isocyanate groups of the polyisocyanate to a total of hydroxyl and amino groups of the polyfunctional nucleophile and chain extender can be 1.5:1, 1.45:1, 1.4:1, 1.35:1, 1.3:1, 1.25:1, 1.2:1, 1.15:1, or 1:1.

In some embodiments, a polyisocyanate described herein comprises an aliphatic, olefinic or aromatic polyisocyanate. The polyisocyanate can have 2, 3, 4, 5, 6, or more isocyanate-groups. In an embodiment, the polyisocyanate is a diisocyanate. The polyisocyanate, for example, can comprise hexamethylene diisocyanate (HDI), isophorone diisocyanate (IPDI), bis(4-isocyanatocyclohexyl) methane, butane diisocyanate (BDI), a lysine diisocyanate, lysine triisocyanate, tris(6-isocyanatohexyl) isocyanurate or any combination thereof. However, other polyisocyanates not inconsistent with the goals of this disclosure are also contemplated.

In some embodiments, a polyfunctional nucleophile described herein is a polyfunctional protic nucleophile. The polyfunctional protic nucleophile can comprise a polyol, a polyamine, or a mercaptan.

A polyol described herein is a compound comprising two or more hydroxyl groups. In some embodiments, a polyol is an oligomer or polymer with multiple terminal hydroxyl groups. A polyol described herein can, for example, comprise poly(ε-caprolactone) (ε-PCL) diol, poly(lactic acid) (PLA) diol, poly(lactic-co-glycolic acid) (PLGA) diol, poly(butylene succinate) (PBS), poly(butylene adipate) (PBA), poly(ethylene glycol) (PEG), poly(propylene glycol) (PPG), poly(tetramethylene ether glycol) (poly(THF)), hydroxyl-terminated polydimethylsiloxane (PDMS), or any combination thereof. However, other polyols not inconsistent with the goals of this disclosure are also contemplated.

In some instances, a polyol described herein can have a weight average molecular weight of 200-10,000, 200-8,000, 200-6,000, 200-4,000, 200-2,000, 200-1000, 200-500, 300-10,000, 400-10,000, 500-10,000, 600-10,000, 700-10,000, 800-10,000, 900-10,000, 1,000-10,000, 2,000-10,000, 3,000-10,000, 4,000-10,000, 5,000-10,000, 6,000-10,000, 7,000-10,000, 8,000-10,000, 500-8,000, 1,000-6,000, or 2,000-4,000.

A polyamine described herein is a compound comprising two or more primary or secondary amine groups. In some embodiments, the polyamine is an oligomer or a polymer with multiple terminal amine groups. Polyamines can, for example, include poly(ethylene glycol) (PEG) diamine, poly(propylene glycol) (PPG) diamine, amine-terminated polydimethylsiloxane (PDMS), or any combination thereof. However, other polyamines not inconsistent with the goals of this disclosure are also contemplated.

The polyamine can have a weight average molecular weight of 200-10,000, 200-8,000, 200-6,000, 200-4,000, 200-2,000, 200-1000, 200-500, 300-10,000, 400-10,000, 500-10,000, 600-10,000, 700-10,000, 800-10,000, 900-10,000, 1,000-10,000, 2,000-10,000, 3,000-10,000, 4,000-10,000, 5,000-10,000, 6,000-10,000, 7,000-10,000, 8,000-10,000, 500-8,000, 1,000-6,000, or 2,000-4,000.

A mercaptan described herein is a compound comprising two or more thiol groups. In some embodiments, the mercaptan is an oligomer or a polymer with multiple terminal thiol groups. Mercaptans can, for example, include poly(ethylene glycol) (PEG) thiol, poly(propylene glycol) (PPG) thiol, thiol-terminated polydimethylsiloxane (PDMS), or any combination thereof. However, other mercaptans not inconsistent with the goals of this disclosure are also contemplated.

The mercaptan can have a weight average molecular weight of 200-10,000, 200-8,000, 200-6,000, 200-4,000, 200-2,000, 200-1000, 200-500, 300-10,000, 400-10,000, 500-10,000, 600-10,000, 700-10,000, 800-10,000, 900-10,000, 1,000-10,000, 2,000-10,000, 3,000-10,000, 4,000-10,000, 5,000-10,000, 6,000-10,000, 7,000-10,000, 8,000-10,000, 500-8,000, 1,000-6,000, or 2,000-4,000.

A chain extender described herein is generally a reactive cross-linking agent that can be used to modify a reaction product produced between the polyisocyanate and the polyfunctional nucleophile. In some instances, the chain extender can be an aliphatic, a siloxane, an ether, or any combination thereof. In some embodiments, the aliphatic, siloxane, and ether chain extenders are a polyamine, a polyol, or any combination thereof. The aliphatic polyamine chain extender, can for example, comprise ethylene diamine, butylene diamine, pentylene diamine, hexamethylenediamine, isophorondiamine, a piperazine, or any combination thereof. The ether chain extender can comprise an amine terminated polypropylene glycol (e.g., JEFFAMINE® D series diamines), an amine terminated polyethylene glycol, or a combination of both. Examples of an aliphatic polyol comprise butanediol, propanediol, hexanediol, cyclohexane dimethanol, or any combination thereof. However, other chain extenders not inconsistent with the goals of this disclosure are also contemplated.

In some embodiments, a solvent described herein comprises water, acetone, ethanol, methyl ethyl ketone, ethanol, isopropanol, methyl acetate, ethyl acetate, butyl acetate, methyl propyl acetate, methyl isobutylketone, tetrahydrofuran, N-methylcyclohexanone, a siloxane, a linear alkane, a branched alkane, a cyclic alkane, or any combination thereof. The linear alkane, branched alkane, and cyclic alkane can, for example, include a linear, branched or cyclic alkane such as propane, butane, pentane, hexane, heptane or octane. Examples of siloxanes comprise hexamethyldisiloxane, octamethyltrisiloxane, hexamethylcyclotrisiloxane, octamethylcyclotetrasiloxane, or any combination thereof. However, the solvents are merely exemplary, and other solvents not inconsistent with the goals of this disclosure are also contemplated.

In some embodiments, solvent described herein is an antimicrobial solvent comprising ethanol, propanol, isopropanol, butanol, isobutanol or any combination thereof. The antimicrobial solvent can be used as the only solvent, or in combination with one or more solvents. Generally, when a thin film is to be applied to a surface of a biologic tissue (e.g., skin), the antimicrobial solvent can sterilize the surface of the biological tissue as the thin film is being formed in situ on the surface. However, these antimicrobial solvents are merely exemplary, and other antimicrobial solvents not inconsistent with the goals of this disclosure are also contemplated.

In some embodiments, a solvent described herein can comprise a first solvent and a second solvent. The first solvent and the second solvent can be chosen from solvents described herein to form a constant evaporating mixture rate that allows the components of the film to remain solvated until the reaction of the film components is complete, without the solvent prematurely evaporating. In some instances, the first solvent and the second solvent can be chosen from the solvents described herein to form a constant evaporating mixture rate that allows one or more polymers in solution to form a homogeneous film without the one or more polymers prematurely precipitating before the solvents are evaporated. While not intending to be bound by theory, it is theorized that the evaporative rate of drying can be controlled by selecting a first solvent and a second solvent that are dissimilar in their chemical properties. For example, solvent combinations can include an alcohol and ketone, alcohol and hydrocarbon, alcohol and acetate, alcohol and ester, acetate and halogenated hydrocarbon, or the like. In some embodiments the evaporation rate is such that the film composition can dry to form a film within 10 minutes, within 8 minutes, within 6 minutes, within 5 minutes, within 4 minutes, within 2 minutes, and within less than 1 minute. In some embodiments, an evaporation rate of solvents are 50-500% (or 0.5-5 folds) of the evaporation rate of n-butyl acetate or 50-500 mmHg*g/mol as described for example by Hofmann in Industrial and Engineering Chemistry, Vol. 24, No. 2, 135-140, the entirety of which is incorporated by reference herein. As noted in Hofmann, the evaporation rate of a liquid is not proportional to the boiling point of the liquid. Moreover, in such instances, an evaporation rate of solvents are 50-400%, 50-300%, 50-250%, 50-200%, 50-150%, 50-125%, 50-100%, 50-75%, 75-500%, 100-500%, 150-500%, 200-500%, 250-500%, 300-500%, 350-500%, 400-500%, 100-400%, 150-350%, or 200-300% of the evaporation rate of n-butyl acetate as described by Hofmann.

In some embodiments, an evaporation rate of the first solvent and an evaporation rate of the second solvent are within 150% of each other, the percentage being based on the larger value. In some instances, an evaporation rate of the first solvent and the second solvent are within 75%, 100%, 115%, 130%, 145%, 160%, 185%, or 200% of each other, the percentage being based on the larger value. For example, in an embodiment, the first solvent comprises ethyl alcohol (EAL) and the second solvent comprises ethyl acetate (EAC). The evaporation rate (ER) can be calculated by Equation 1, as disclosed in Hofmann:

$$\text{Evaporation Rate} = \text{Vapor pressure} * \text{Molecular weight} / 11 \quad \text{(Eq. 1)}$$

For ER of ethyl alcohol (EAL)=43.7 mmHg×46.07 g/mol/11=183.02 mmHg*g/mole; ER of ethyl acetate (EAC), 73.91 mmHg×88.11 g/mol/11=389.95 mmHg*g/mol. Both solvents therefore have an evaporation rate within 150% of each other and within 50 to 1500% of the references n-butyl acetate (ER of n-butyl acetate is 100 mmHg*g/mol at 20° C.).

In some embodiments, the mixture of the first solvent and the second solvent can have a polarity index of 1 to 7. In some instances, the polarity index is 2 to 6 or 3 to 5. In some cases, the polarity index is 1, 2, 3, 4, 5, 6, or 7. The polarity index of the mixture can be calculated according to Equation 2. According to Poole, C. F.; Poole, S. K. Chromatography Today; Elsevier: Amsterdam, 1991, the polarity index P' of a mixed mobile phase is the arithmetic average of the solvent polarity index weighting factor adjusted according to the volume fraction of each solvent as is given by Equation 2:

$$P = \Sigma_i P'_i \emptyset_i \quad \text{(Eq. 2)}$$

where $P'_i$ is the polarity index weighting factor of solvent I, and $\emptyset_i$ is the volume fraction of solvent i. For example, for a binary solvent mixture containing 30% ethyl alcohol (EAL) and 70% ethyl acetate (EAC), the polarity index of the mixed solvent is calculated as follows:

$$P' = (5.2)(0.3) + (4.4)(0.7) = 4.64$$

In some embodiments, the mixture of the first solvent and the second solvent can have a dielectric constant of 2 to 30. In some instances, the dielectric constant of the mixture is 5 to 25, 10 to 20, 12 to 18, 5 to 15, 5, 8, 10, 12, 14, 16, 18, 20, 22, 24, 26, 28, or 30. The value of the dielectric constant of the mixture can be calculated by multiplying the volume fraction of each solvent times its dielectric constant and summing, as illustrated by Equation 3:

$$A + B = f_A \delta_A + f_B \delta_B + \ldots \quad \text{(Eq. 3)}$$

wherein A and B are the solvents in the mixture, f is the volume fraction of each solvent, and c is the dielectric constant of each solvent. For example, for a mixture of ethyl alcohol ($\delta$=24.5) and ethyl acetate ($\delta$=6.02), the dielectric constant of an EAL/EAC (3:7) mixture can be calculated as follows:

$$\text{mixture of EAL/EAC}(3:7) = 24.5*0.3 + 6.02*0.7 = 11.56.$$

Raoult's law states that the partial vapor pressure of each component of an ideal mixture of liquids is equal to the vapor pressure (VP) of the pure component multiplied by its mole fraction in the mixture. In some embodiments, the mixture of the first solvent and the second solvent has a total vapor pressure of 4 to 80 mmHg according to Raoult's law. In some instances, the mixture of the first solvent and the second solvent has a total vapor pressure of 10 to 40 mmHg, 20 to 30 mmHg, 15 to 30 mmHg, 4 mmHg, 8 mmHg, 10 mmHg, 15 mmHg, 20 mmHg, 25 mmHg, 30 mmHg, 35 mmHg, 40 mmHg, 45 mmHg, 50 mmHg, 55 mmHg, 60 mmHg, 75 mmHg, or 80 mmHg according to Raoult's law. As an example, using a 3:7 volume ration of EAL (VP=43.7 mmHg) to EAC (VP=73.91 mmHg), the molar ratio of EAL=0.273 and the molar ratio of EAC=0.727. The Total vapor pressure of EAL/EAC=43.7*0.273+73.91*0.727=65.66 mmHg.

In some embodiments, a thin film described herein is elastomeric and has a strain rate (e.g. elongation rate at break) of 100% to 1200%. For example, the strain rate at break for the film can be at least greater 100%, greater than 200%, greater than 300%, greater than 400%, greater than 500%, or greater than 600%. The elastomeric nature of the film assists the film in remaining adhered to a flexible surface. For example, when the film is placed on human or animal skin, the film can stretch and bend with the skin, allowing the film to flexibly mimic the motions of the skin. Additionally, the elastomeric nature of the film imparts, as seen below in FIGS. 1-4, an ability to peel the film from the substrate surface.

The thickness of a thin film described herein can vary depending on the application. For example, in some embodiments, a film has an average thickness of 20 to 300 microns. In other embodiments, the film has an average thickness of 20 to 50 microns, 20 to 100 microns, 20 to 150 microns, 20 to 200 microns, or 20 to 250 microns.

In some embodiments, a thin film described herein can have a water vapor transmission rate of 200 to 600 g/m²/day. In other embodiments, the film has a water vapor transmission rate of 200 to 400 g/m²/day, 300 to 500 g/m²/day, 400 to 600 g/m²/day, 500 to 600 g/m²/day, 200 g/m²/day, 300 g/m²/day, 400 g/m²/day, 500 g/m²/day, or 600 g/m²/day. The water vapor transmission rate of the film can be determined according to ASTM standard test method E96/E96M-15, described in more detail below in Example 4. For substrates such as human or animal skin, the water vapor transmission values of the film can in some cases allow for sweat to evaporate off of the skin and be released to the atmosphere through the film rather than being trapped between the skin and the film.

Young's modulus (e.g. the elastic modulus) is a mechanical property of elastic solid materials that defines a relationship between stress (force per unit area) and strain (proportional deformation) in a material. In some embodiments, a thin film described herein have a Young's modulus of 3 to 20 MPa. In other embodiments, the film has a Young's modulus of 4 to 18 MPa, 6 to 16 MPa, 8 to 14 MPa, 10 to 12 MPa, 5 to 17 MPa, 7 to 15 MPa, 9 to 13 MPa, 3 to 10 MPa, 10 to 15 MPa, 15 to 20 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, or 20 MPa. Young's modulus values of the film can be determined according to ASTM standard test method D882, described in more detailed below in Example 6.

Tensile strength at break is a resistance of a material to breaking under tension. In some embodiments, the film has a tensile strength of 10 to 60 MPa. In other embodiments, the film has a tensile strength of 10 to 50 MPa, 10 to 40 MPa, 10 to 30 MPa, 10 to 20 MPa, 20 to 60 MPa, 30 to 60 MPa, 40 to 60 MPa, 50 to 60 MPa, 20 to 50 MPa, 30 to 40 MPa, 10 MPa, 15 MPa, 20 MPa, 25 MPa, 30 MPa, 35 MPa, 40 MPa, 45 MPa, 50 MPa, 55 MPa, or 60 MPa. Tensile strength values of the film can be determined according to ASTM standard test method D882, described in more detailed below in Example 6.

In some embodiments, a thin film described herein has a molecular weight of $1.0 \times 10^4$ g/mol to $5.0 \times 10^5$ g/mol. In other embodiments, the film has a molecular weight of $5.0 \times 10^4$ g/mol to $5.0 \times 10^5$ g/mol, $1.0 \times 10^5$ g/mol to $5.0 \times 10^5$ g/mol, $2.5 \times 10^5$ g/mol to $5.0 \times 10^5$ g/mol.

ISO 10993 sets forth a series of standards for evaluating biocompatibility of medical devices. In some embodiments, according to the series of standards described in ISO 10993, a thin film described herein is non-cytotoxic, has implantation compatibility, is non-pyrogenic, is a non-irritant, is non-sensitizing, does not exhibit systemic toxicity, or any combination thereof. Particular examples of the film conforming to one or more of the series of standards described in ISO 10993 are described in more detail below in Examples 10 to 14.

In some embodiments, a thin film described herein forms a microbial barrier when the film is disposed on a substrate surface. The microbial barrier refers to a film forming a barrier that prevents, excludes, or reduces microbial penetration. The microbial penetration can be in one direction or both directions. For example, microbial penetration can be through the film from the substrate surface in an outward direction away from the substrate surface, or can be through the film from an outer surface of the film in an inward direction towards the substrate surface. In some embodiments, the film forms a microbial barrier that prevents 80% to 100%, 90%-100%, 80%, 90%, or 100% of microbe penetration.

In some embodiments, a film forming composition and a thin film described herein comprises an additive. Exemplary additives comprise an antimicrobial agent, growth factors, peptides, therapeutic agents, anti-inflammatory agents, analgesic agents, biological regenerative agents, cosmetic agents, a metal anti-oxidant, or any combination thereof. For example, the antimicrobial agent can comprise an antibiotic, antifungal, or other pharmaceutically acceptable antimicrobial agent. Exemplary cosmetic agents include a coloring agent or dye, such as mica, iron oxide, manganese violet, zinc oxide, or other known cosmetic dyes or pigments to match the thin film to the substrate (e.g., flesh-colored dyes to match human skin tones). Exemplary growth factors include vascular endothelial growth factor (VEGF), platelet-derived growth factor (PDGF), neurotrophins, keratinocyte growth factor (KGF), insulin-like growth factor (IGF), fibroblast growth factor (FGF), epidermal growth factor (EGF), angiopoietin, erythropoietin or any known growth factors that may be incorporated into the films for wound treatment. Exemplary peptides include MG53, RGD, RGDFV, RGDS, or any known peptides that can be incorporated into the films for wound treatment.

II. Method of Forming a Film

In another aspect, methods of forming a film on a substrate are described herein, which, in some embodiments, can offer one or more advantages over other methods of forming a film on a substrate. For example, in some embodiments, the method of forming the film described herein is simple, efficient, scalable, inexpensive, reproducible, compatible with biological tissue, and/or has desirable physical properties. Particularly, the method of forming the film described herein can be formed in situ (e.g., formed "in place") on a substrate, such as skin.

In some embodiments a method of forming a film on a surface of a substrate comprises applying the polyisocyanate, the polyfunctional nucleophile, and the chain extender to the substrate. In some embodiments, the polyisocyanate and the polyfunctional nucleophile are first combined to form a pre-polymer, and the chain extender is subsequently combined with the formed pre-polymer. Each of the polyisocyanate, the polyfunctional nucleophile, and the chain extender can be applied to the surface of the substrate neat or in combination with a solvent. In some embodiments, the polyisocyanate, polyfunctional nucleophile, and chain extender can be combined together and reacted in the chosen solvent(s) to produce a thin-film forming polymer solution before the polymer solution is applied to a substrate to form the thin film.

In some embodiments, methods described herein can further comprise applying an additive to the surface of the substrate. The additive can be applied to the surface of the substrate at any step of the method. In some instances, the additive can be combined with one or more of the polyisocyanate, the polyfunctional nucleophile, or the chain extender, or the final polymer solution and applied to the surface of the substrate. In a non-limiting example, when the additive is an antibiotic, the antibiotic can be combined with the polyisocyanate or the polyfunctional nucleophile, and be applied to the substrate as a combination with that component. In this example, the antibiotic would be incorporated into the resulting pre-polymer matrix prior to the addition of the chain extender. In another non-limiting example, the antibiotic can be combined with the chain extender, and become incorporated in the resulting polymer matrix forming the thin film. In another non-limiting example, the antibiotic can be combined with the final polymer solution and become incorporated in the thin film formed on a substrate. In yet another non-limiting example, the antibiotic can be applied directly to the surface of the substrate, and the resulting thin film be formed over the antibiotic, effectively forming an antibiotic layer between the substrate and the thin film.

The components of the film can be applied to the surface of the substrate in various formulations, such as in the form of a liquid, cream, lotion, emulsion, or other formulation. The method can be performed by applying each component with an applicator (e.g., a brush) or by hand application. Each component can also be applied by a spray or aerosol, or by dipping the substrate into each component.

The characteristics and type of the polyisocyanate, the polyfunctional nucleophile, the chain extender, the optional solvents, and the optional additives are understood to be consistent with the description for each component in Section I.—Film Composition previously discussed herein.

III. Exemplary Applications for the Film

A thin film and method of forming a thin film on a substrate described herein can have applications in a number of different fields, including human health care, industrial equipment, veterinary care, cosmetics, art, cinema, and athletics industries. For each of the following exemplary applications for the film, it should be appreciated that each is for the purpose of illustrating aspects of the invention, and does not limit the scope of the invention as defined in the claims.

In one example, such as in the healthcare and cosmetic fields, a thin film can be applied to a prosthetic device using a film composition and method described herein such that prosthetic device receives a film coating. The film can include an additive such as a coloring agent, dye, or pigment so that the film visually resembles a specific skin tone.

In another example, a thin film described herein can be applied to a robotic instrument or gripping tool using a spray system. The sprayed film can in some cases provide an enhanced grip, an aesthetic benefit, or a human-like feature. The film can be applied using several coats and can be replenished as wear occurs. Exemplary robotic instruments can include those used for picking fruit, assembling delicate hardware, or performing robotic medical procedures.

In another example, a thin film described herein can be used to protect the mammary glands of dairy animals from pathogenic contamination by forming a teat sealant over the teat of the dairy animal to decrease the incidence of mastitis in the animals.

A thin film described herein can be used to cover a humanoid robot or companion doll to make it more life-like, comfortable, or natural. This includes robots, androids, or automaton built for social, commercial, and industrial use. While the film can be used to form a skin-like film, the film can also be used to conceal or protect mechanical aspects or sensitive parts of the humanoid robot.

Another industrial application of a thin film described herein is a waterproof or atmospheric barrier to cover a surface of a metallic component to reduce exposure of the surface to water or oxygen, reducing rust formation (e.g., metal oxidation), and prolonging the lifetime of the material. For example, the metallic component can be part of a marine vessel that is often exposed to highly oxidative conditions. In some cases, anti-oxidation properties of the film can be enhanced by including a metal antioxidant additive, as previously discussed above.

Thin films described herein can have various applications involving biological tissue, both human and animal. For example, the film can mimic skin, and be applied to compromised skin having minor cuts, cracks, scrapes, burns, blisters and closed surgical incisions and excisions to protect these features from external bacteria and dirt, and to possibly reduce pain and itching by covering nerve ends. The film can also be applied to protect or soothe the skin from problems such as dryness, itching, blistering, or peeling of patients who receive radiation therapy and are unable to tolerate regular bandages, tapes or skin protectants. The film can naturally slough off over time or be peeled off of the skin when needed and can be re-applied as a new film or before the original film sloughed off or peeled off.

In another example, a thin film described herein can be applied to the chest of a long-distance runner to provide a barrier that reduces friction between the chest and garments, preventing chafing and irritation.

In yet another example, a thin film described herein can be applied to a dermal access of a catheter to secure or seal the catheter. The film can also be applied to a surface of a dermal area adjacent to a catheter port. Upon catheter insertion, securing tape is applied to the surface of the dermis protected by the film. Upon physical removal of the securing, adhesive tape, the film prevents the subject's dermis from damage.

A thin film described herein can be applied to dermal folds of an obese individual and allowed to persist for certain period of time, such as up to 24 hrs. The film acts as a barrier between contact points of separate skin folds, where it reduces friction and keeps the dermal area dry and comfortable until the film is naturally sloughed off or later removed with soap and water.

A thin film described herein can be applied to the external, dermal area of a joint, such as the elbow, and minimizes abrasions that can occur during exercise or sporting activities.

A thin film described herein can be applied to border of a stoma and prevents the irritation and sensitization of healthy tissue that can be affected by ostomy leak.

A thin film described herein can be applied to the thighs and buttocks of an elderly or immobilized individual and reduces irritation and chafing that can accompany incontinence.

A thin film described herein can be used as a surgical drape and microbial sealant during surgery, where it can be applied by a physician. The applied film can laminate the flora of a patient's dermis and reduces the likelihood of the flora entering a surgical incision and causing an infective complication.

A thin film described herein can be applied to a foot of a diabetic patient to enhance the mechanical strength of the natural dermis, reducing the rate of ulcer formation and preventing the formation of painful sores.

A thin film described herein can be applied the skin areas that are prone to develop or have already developed bedsores or pressure ulcer to prevent or reduce ulceration, pus-like draining, pain, and swelling.

In another example, a thin film described herein can be applied to the forearm of an individual, forming a barrier capable of protecting against abrasions.

In another example, a thin film described herein can be applied to open sores on cattle suffering from an outbreak of foot and mouth disease. Spot checks of the livestock identify blistering individuals likely to contribute to and propagate the spread of infection. The film can be applied on the wound to reduce further spread of disease.

Some embodiments described herein are further illustrated in the following non-limiting examples.

Example 1

Synthesis of Thin Film-1

A polymer formulation was synthesized using monomers isophorone diisocyanate/piperazine/polycaprolactone diol with a molar ratio of 2/1/1 in a glass reactor quipped with a dry nitrogen/vacuum line, controlled heating apparatus and stirring mechanism. At 45° C., isophorone diisocyanate was slowly added to dried polycaprolactone diol and reacted in acetone solvent until the desired isocyanate content was reached. This mixture was also reacted in other skin-compatible solvents, including acetone, ethanol, tetrahydrofuran, isopropanol, methyl acetate, ethyl acetate, n-butyl acetate, isobutyl acetate or mixture of solvents, until the desired isocyanate content was reached. Then piperazine was added dropwise to the mixture at room temperature and additional solvent or mixture of solvents was added to form a clear and viscous polymer solution.

Example 2

Synthesis of Thin Film-2

A polymer formulation was synthesized using monomers isophorone diisocyanate/polycaprolactone diol/polyethylene glycol/isophorondiamine/with a molar ratio of 2.4/0.2/1.2/1 in a glass reactor quipped with a dry nitrogen/vacuum line, controlled heating apparatus and stirring mechanism. At 45° C., isophorone diisocyanate was slowly added to a dried polycaprolactone diol/polyethylene glycol mixture and reacted in different skin-compatible solvents, including acetone, ethanol, tetrahydrofuran, isopropanol, methyl acetate, ethyl acetate, n-butyl acetate, isobutyl acetate, and mixtures thereof, until the desired isocyanate content was reached. Isophorondiamine was then added dropwise into the reactor at room temperature and additional solvent or mixture of solvents was added to form a clear and viscous polymer solution.

Example 3

Drying Time for Thin Films

Thin Film formulations prepared according to EXAMPLE 1 were painted on a glass slide at 35° C. to evaluate the drying time. All samples showed a quick drying within 2 minutes, and formed transparent and homogeneous films after drying. The average drying time for different polymer concentrations is listed in Table 1.

TABLE 1

Average Drying Time of a Thin Film Prepared in EXAMPLE 1 at Different Concentrations

| EXAMPLE 1 Thin Film (concentration (% wt)) | Average Drying Time (Seconds) |
|---|---|
| 10 | 98 ± 4 |
| 15 | 84 ± 4 |
| 20 | 71 ± 2 |
| 25 | 47 ± 2 |
| 31 | 34 ± 2 |

Example 4

Water Vapor Transmission Rate of Thin Films

The ability of water vapor to pass through a thin film described herein was measured as a water vapor transmission rate (WVT) according to ASTM standard test method E96/E96M-15. The WVTs were evaluated for polymer formulations prepared according to EXAMPLE 1 and EXAMPLE 2, and determined to be 545.6 g/(day)(m$^2$) and 657.0 g/(day)(m$^2$) respectively, which are comparable to the water vapor transmission rate in human skin, 240-1920 g/(day)(m$^2$).

Example 5

Water Absorption and Contact Angle

Performance of thin films described herein under wet condition were evaluated by measuring contact angle, surface energy and water absorption. Thin films prepared from EXAMPLE 1 and EXAMPLE 2 formulations exhibited abilities to form hydrophobic and waterproof films, and showed low water absorption rates, as shown in Table 2.

TABLE 2

Performance of Thin Films Under Wet Conditions

| | Contact Angle (°) | | Surface Energy (mJ/m$^2$) | Water Absorption (%, 7 days) |
|---|---|---|---|---|
| | De-ionized Water | Diiodomethane | | |
| EXAMPLE 1 | 88.2 | 33.2 | 42.9 | 20.09 |
| EXAMPLE 2 | 85.1 | 28.4 | 45.0 | 30.94 |

Example 6

Mechanical Properties

The mechanical properties for the thin film formulations prepared according to EXAMPLE 1 were evaluated according to a standard method ASTM D882, and are shown in Table 3.

TABLE 3

Mechanical Properties of Thin Films

| Formulation | Tensile Stress (MPa) | Initial Modulus (MPa) | Strain (%) |
|---|---|---|---|
| 1 | 26.03 ± 5.52 | 6.71 ± 1.07 | 616.67 ± 39.92 |
| 2 | 16.77 ± 3.7 | 6.57 ± 0.71 | 514.92 ± 40.07 |
| 3 | 42.13 ± 7.3 | 8.38 ± 0.77 | 559.81 ± 52.16 |

Indicated by above mechanical properties, the thin film formulations prepared according to EXAMPLE 1 were able to form elastic and flexible, but tough polymer films.

Example 7

In Situ Film Formation on Skin

Film compositions prepared according to EXAMPLE 1 and EXAMPLE 2 were applied on human skin including forearm, leg and knuckles. The formed transparent films had a thickness of 20~120 μm upon curing, with curing time being within 2 minutes. As shown in FIGS. 1-4, the formed films are flexible and peelable from human skin and fingernail. The films were observed to stay on the skin for more than 2 days without edge-up. No crack formation was observed. The films remained intact on the skin and no edge-up was observed after taking shower or swimming.

Figure 2:
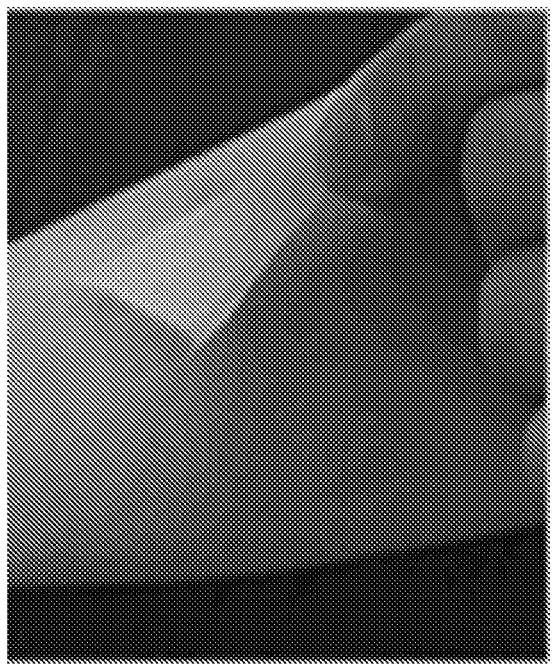
FIG. 2 is a photo the thin film of FIG. 1 being peeled off of the skin.
Figure 3:
FIG. 3 is a photo of an exemplary thin film applied to a fingernail.
Figure 4:
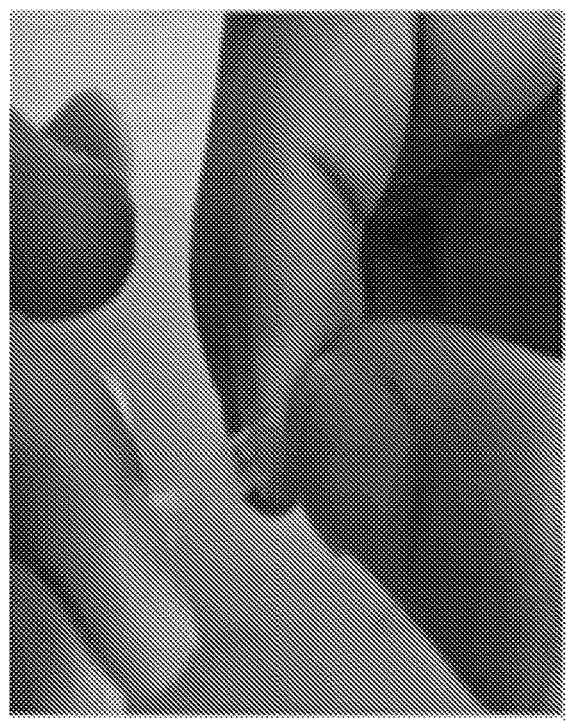
FIG. 4 is a picture of the thin film of FIG. 3 being peeled off the fingernail.

It was observed that the film being peeled from the fingernail in FIG. 4 was transparent, and the film being peeled from skin in FIG. 2 was opaque. While not intending to be bound by theory, it is believed that the solvent systems in the thin film forming solution may be dissolving/clearing the skin surface lipid film (SSLF), a mixture of sebum from the sebaceous glands and lipids secreted by keranocytes, during film formation to facilitate strong skin adhesion. Consequently, sebum and lipids imprinted on the film in FIG. 2 is likely causing the opaqueness.

Example 8

Bacterial Barrier

A study was conducted to evaluate the ability of thin film formulations prepared according to EXAMPLE 1 to act as a protective barrier to prevent microbial penetration. The formulations were brushed on agar plates and allowed to form a polymer film in-situ. Each of five (5) clinically relevant microorganisms, listed as below, was directly deposited on the formed films. Then the dishes were incubated in conditions favoring these microorganisms' growth. At 1 and 3 days, dishes were evaluated for colony-forming-units underneath the films. If any microbe penetrated through the polymer film, it would form a colony underneath the film. The study showed that formulations from Example 1 formed 100% effective microbial barrier for all five microbes. The five clinically relevant microorganisms included *Staphylococcus aureus* (*S. aureus*, ATCC No. 6538); *Escherichia coli* (*E. coli*, ATCC No. 8739); *Pseudomonas aeruginosa* (ATCC No. 9027); *Candida albicans* (*C. albicans*, ATCC No. 10231); and *Aspergillus brasiliensis* (ATCC No. 16404).

Example 9

Antimicrobial

An antimicrobial study, following U.S. Pharmacopeia Chapter 51—Antimicrobial Effectiveness Testing, was done to evaluate the antimicrobial properties of the formulations prepared according to EXAMPLE 1 and EXAMPLE 2. The five (5) microorganisms listed in Example 6 were used to challenge the samples. Both EXAMPLE 1 and EXAMPLE 2 exhibited antimicrobial properties towards all five microbes under the U.S. Pharmacopeia Chapter 51 standards.

A further study was conducted to evaluate the antimicrobial property of EXAMPLE 1 formulations under multiple-use scenarios. During a 10-day period, the formulations were repeatedly challenged each daily by the above five microbes, each with a concentration of $1 \times 10^6$ to $1 \times 10^7$ CFU. The formulations were found to retain its antimicrobial property over the course of multiple-challenging. following the standards described in U.S. Pharmacopeia Chapter 51.

Example 10

Cytotoxicity

Formulations prepared according to EXAMPLE 1 were evaluated for cytotoxicity according to the standard ISO 10993-5: Tests for In-vitro Cytotoxicity. Two assays, Agarose Overlay and Direct Contact using mouse fibroblast cells were conducted. The formulations were scored as non-toxic in both assays.

Example 11

Skin Irritation and Sensitization

Formulations prepared according to EXAMPLE 1 were evaluated for skin irritation and sensitization according to the standard ISO 10993-10: Tests for Irritation and Skin Sensitization. Buehler Dermal Sensitization Test were conducted on albino guinea pigs to evaluate the formulations for any allergic reactions such as erythema and edema. Each study showed that the formulations did not elicit any sensitization responses.

The formulations were additionally applied directly on shaved rabbits to evaluate dermal irritation potential. The primary irritation index of the formulations was scored as 0.2, indicating negligible irritation response.

Example 12

Subcutaneous Implantation

Formulations prepared according to EXAMPLE 1 were evaluated for their local effects when in direct contact with living subcutaneous tissue of rabbits according to the standard ISO 10993-6 Tests for local effects after implantation. The conducted subcutaneous implantation with histopathological analysis scored the formulations an irritant ranking score of 0.0, indicating the formulations were non-irritants.

Example 13

Acute Toxicity

Formulations prepared according to EXAMPLE 1 were evaluated for short-term systemic toxic effects in mice according to the standard ISO 10993-11: Tests for Systemic Toxicity. No signs of toxicity were observed in any mice treated with the formulations, indicating the formulations are non-toxic.

Example 14

Subchronic Toxicity

A two-week subchronic toxicity study in rats was conducted according to the same ISO standard method in EXAMPLE 13 to evaluate the EXAMPLE 1 formulations for long-term systemic toxic effects. Clinical observations, tissue histopathological analysis, blood hematology, coagulation, clinical chemistry and gross necropsy were conducted in the study. The formulations were determined to be negative for any signs of systemic toxicity.

Example 15

Comparative Data: Run Away During Application

Figure 5:
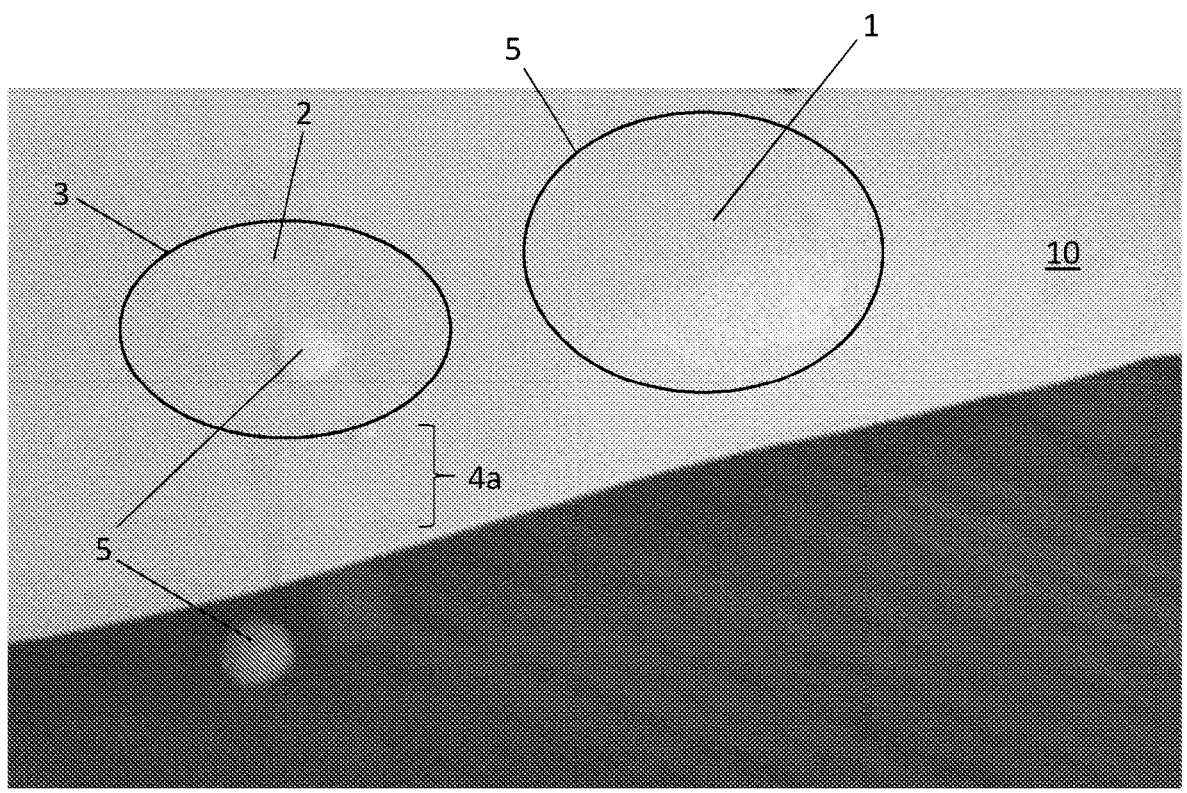
FIG. 5 is a picture of KeriCure® run away compared to an absence of run away of an exemplary thin film.

A formulation prepared according to EXAMPLE 1 (Thin film 1) and the commercially available KeriCure® was applied to human skin. As previously described herein, KeriCure® is a water-based polyacrylate emulsion solution marketed for skin application. As shown in FIG. 5, KeriCure® 2 upon application to human skin 10, beads up and "runs away" to form streaks 4a and beading 4b away from an original application location 3. The streaks 4a and beading 4b of KeriCure® 2 are partially attributable to a long curing time of >5 min and a low viscosity. Additionally, the low viscosity of KeriCure® 2 resulted in a very thin film that was nearly invisible, and failed to provide any sensation of protection. In contrast, thin film 1 forms nearly an invisible thin film confined to an original application location 5, with a cure time of approximately 2-3 minutes.

Example 16

Comparative Data: Film Cracking and Peelability

A formulation prepared according to EXAMPLE 1 (Thin film 1), commercially available KeriCure®, and commercially available New Skin® was applied to human skin and cracking was monitored form each after 5 min, 8 hrs, 18 hrs, and 24 hrs. Additionally, an ability of each to be removed by peeling was determined after 24 hrs. As previously described herein, New Skin® is an organic solvent-based solution composed of nitrocellulose and ethanol/acetate/acetone solvents marketed for skin application.

Figure 6A:
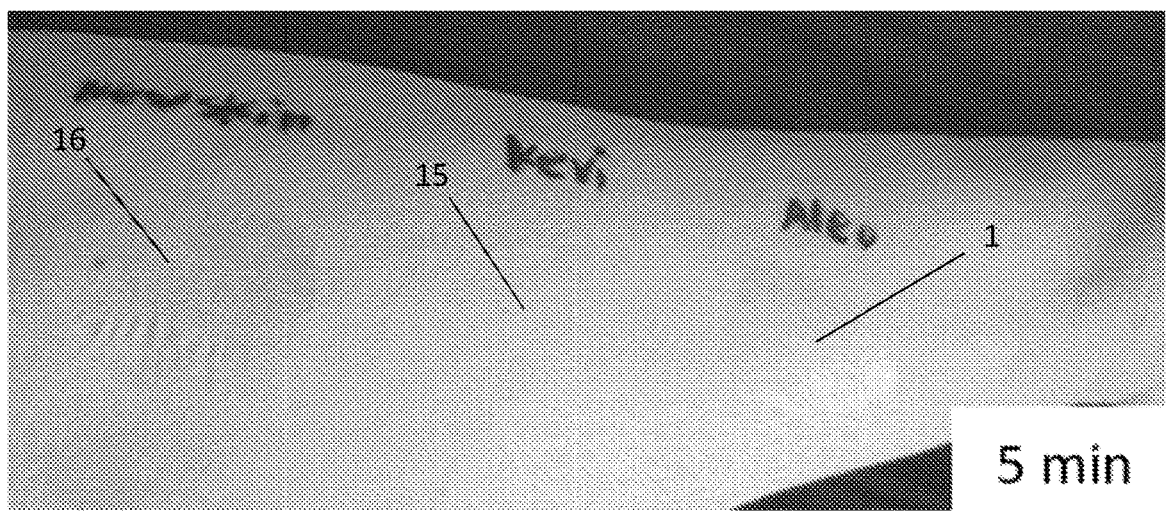
FIG. 6A is a picture of an exemplary thin film, KeriCure®, and New Skin® 5 minutes after application to human skin.

FIG. 6A is a picture of thin film 1, KeriCure® 15, and New Skin® 16 taken 5 minutes after application to human skin 10. As shown, thin film 1 and New Skin® 16 formed visible films, with New Skin® 16 displaying some peripherally-located wrinkles due to shrinkage during curing/drying. Thin film 1 displayed little to no wrinkles. As previously described in EXAMPLE 15, KeriCure® 15 forms a very thin film that is nearly invisible on the skin 10.

Figure 6B:
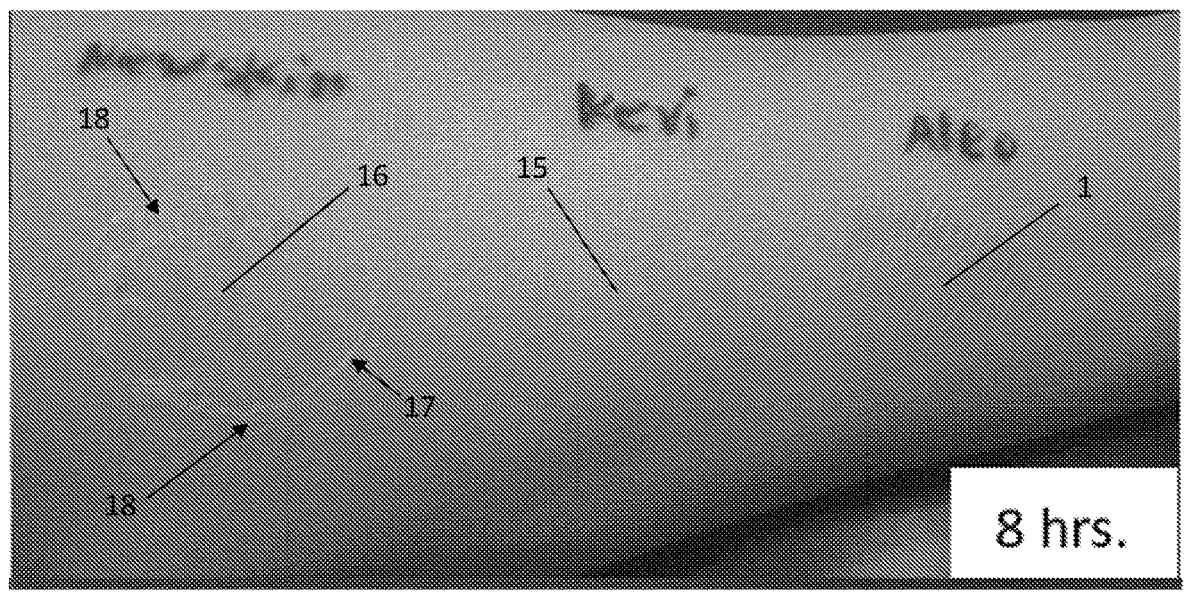
FIG. 6B is a picture of the exemplary thin film, KeriCure®, and New Skin® of FIG. 6A 8 hours after application to human skin.

FIG. 6B is a picture of thin film 1, KeriCure® 15, and New Skin® 16 following 8 hours after application to human skin. As shown, thin film 1 showed slight wrinkling, but no edging was observed around the periphery of the film. In contrast, New Skin® 16 film showed clear edging 17 around the entire periphery of the film, and cracking 18 was also observed in areas of the film near the periphery. The KeriCure® 15 film was still nearly invisible, and it was observed that most, if not all, of the film had flaked or rubbed off at this time.

Figure 6C:
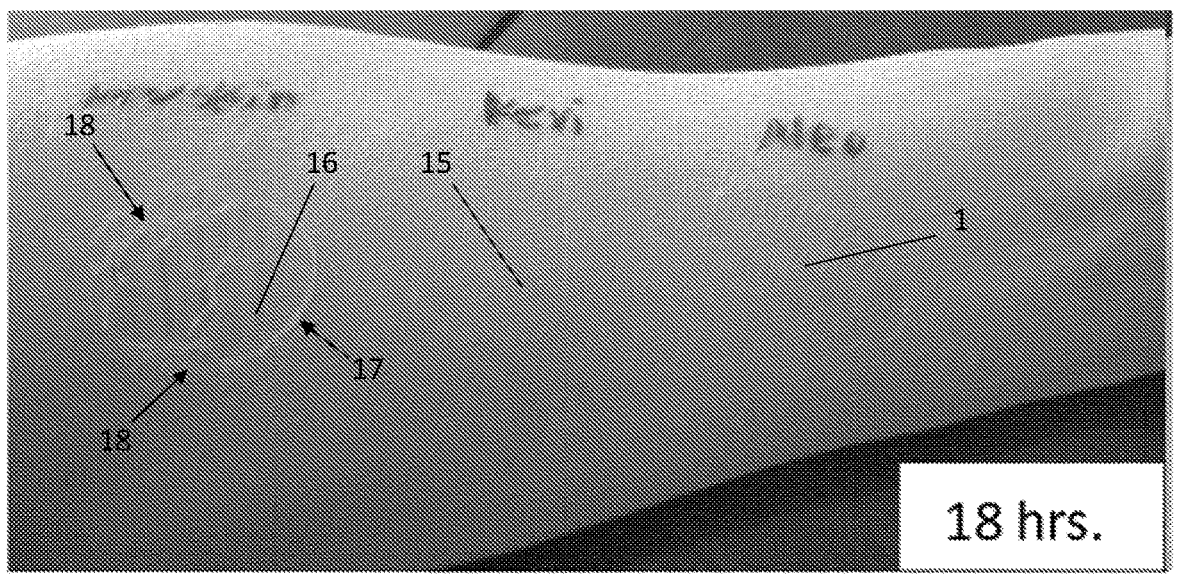
FIG. 6C is a picture of the exemplary thin film, KeriCure®, and New Skin® of FIG. 6A 18 hours after application to human skin.

FIG. 6C is a picture of the exemplary thin film, KeriCure®, and New Skin® of FIG. 6A taken 18 hours after application to human skin. As shown, thin film 1 continued to show the same amount of slight wrinkling observed in FIGS. 6A and 6B. However, no cracking was observed, and only a very minimal amount of edging is visible. In contrast, the New Skin® 16 film displayed more pronounced edging 17 and cracking 18 in areas around the periphery of the film. Additionally, large cracks 18 were observed in the central regions of the film.

Figure 6D:
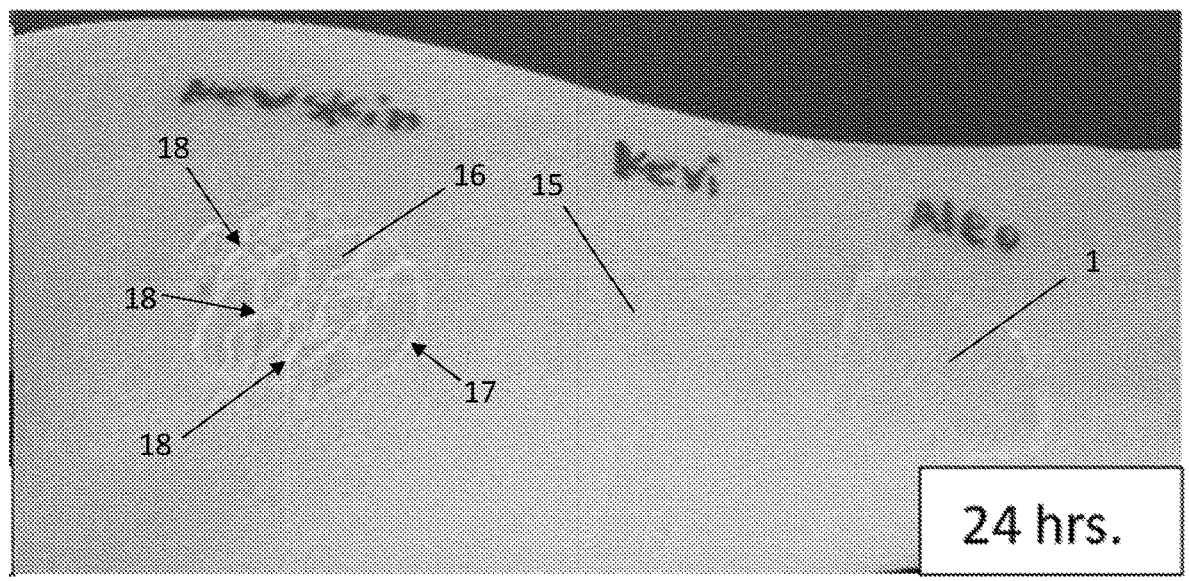
FIG. 6D is a picture of the exemplary thin film, KeriCure®, and New Skin® of FIG. 6A 24 hours after application to human skin.

FIG. 6D is a picture of the exemplary thin film, KeriCure®, and New Skin® of FIG. 6A taken 24 hours after application to human skin. As shown, thin film 1 continued to show the same amount of slight wrinkling observed in FIGS. 6A-6C. Thin film 1 did display some visible edging, however, no cracking was observed. In contrast, the New Skin® 16 film displayed extensive cracking 18 throughout the entire film, and each of the cracks 18 individually showed considerable edging 17.

Figure 7:
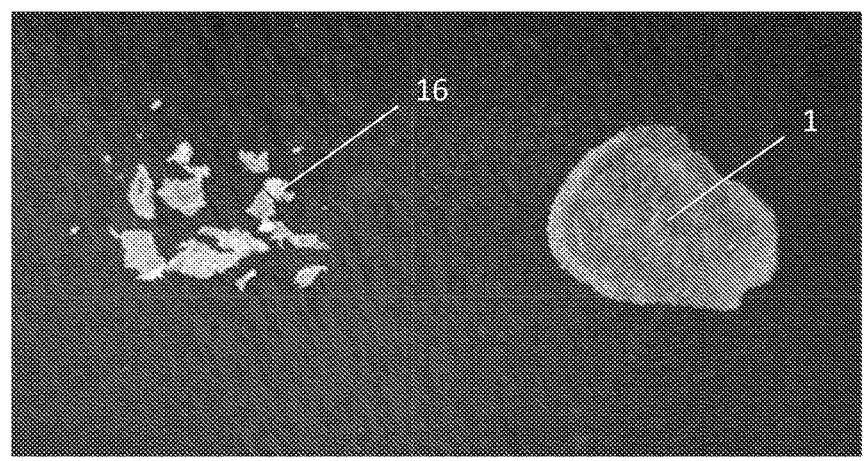
FIG. 7 is a picture of the exemplary thin film and New Skin® of FIG. 6A after removal from human skin.
Figure 8:
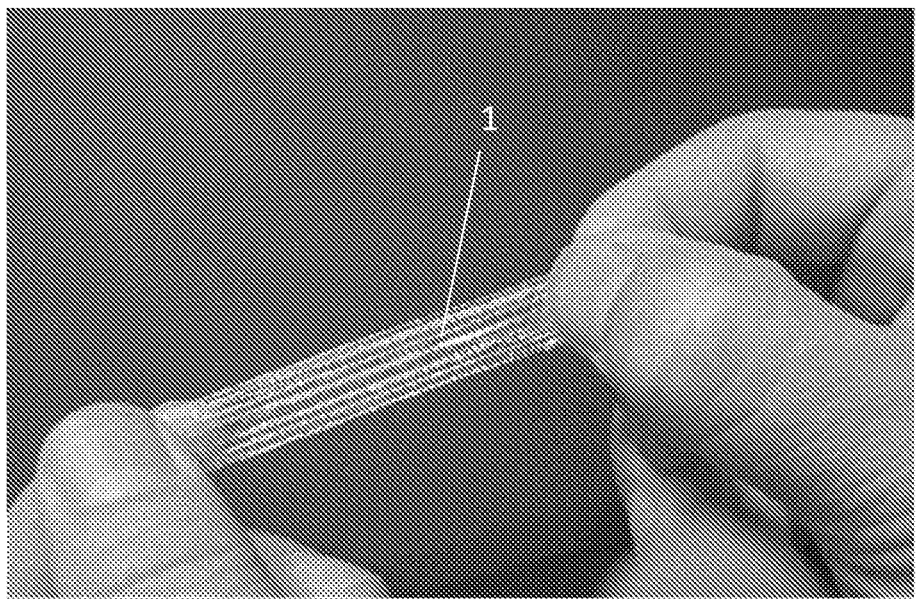
FIG. 8 is a picture of the exemplary thin film of FIG. 7 being stretched after removal from human skin.

FIG. 7 is a picture of the exemplary thin film and New Skin® of FIG. 6A after removal from human skin. As shown, thin film 1 was easily removed by peeling (see e.g. FIG. 2), and was removed as a single piece of elastic material. FIG. 8 shows thin film 1 of FIG. 7 being stretched after removal. In contrast, New Skin® 16 film was only removable from the skin in pieces, and each of the removed pieces was brittle, lacking elasticity (FIG. 7).

Consequently, exemplary thin film 1 can be formed in situ on a surface, and exhibit desirable elastic, peelable, and/or durable physical properties, such as being applicable to skin without "run-away", and being quickly formed upon application. In some instances, thin films described herein have sufficient skin adhesion strength to adhere on skin at least 1+ days without edging up, or with minimal edging, while still retaining the ability to be peeled as an intact film like a regular bandage for easy removal when needed. Furthermore, exemplary thin film 1 provides a good sensation of protection like a regular bandage, but be transparent without crack formation.

Example 17

Comparative Data: Solvent Effects

A formulation was prepared according to EXAMPLE 1 (Thin film 1) except that two different solvent systems were used to illustrate the effects of different solvent combinations on the adherence of the thin film to skin. A first formulation 20 was prepared according to EXAMPLE 1 using a solvent system comprising a mixture of methyl acetate (40 mL) and isopropanol (50 mL). Methyl acetate has an evaporation rate of 6.0, where n-butyl acetate is used as a standard with an evaporation rate of 1.0. Isopropanol has an evaporation rate of 1.7, where n-butyl acetate is used as a standard with an evaporation rate of 1.0. The evaporation rate of methyl acetate to isopropanol is $(6.0/1.7) \times 100 = 353\%$. Thus, the evaporation rate of methyl acetate and the evaporation rate of isopropanol are much greater than 150% of each other, where the percentage is based on the larger evaporation value.

A second formulation 30 was also prepared according to EXAMPLE 1 using a solvent system comprising a mixture of isopropanol (30 mL) and isobutyl acetate (70 mL). As previously stated, isopropanol has an evaporation rate of 1.7. Isobutyl acetate has an evaporation rate of 1.4, where n-butyl acetate is used as a standard with an evaporation rate of 1.0. The evaporation rate of isopropanol to isobutyl acetate $(1.7/1.4) \times 100 = 121\%$. Thus, the evaporation rate of isopropanol and the evaporation rate of isobutyl acetate are within 150% of each other, the percentage being based on the larger value.

Figure 9:
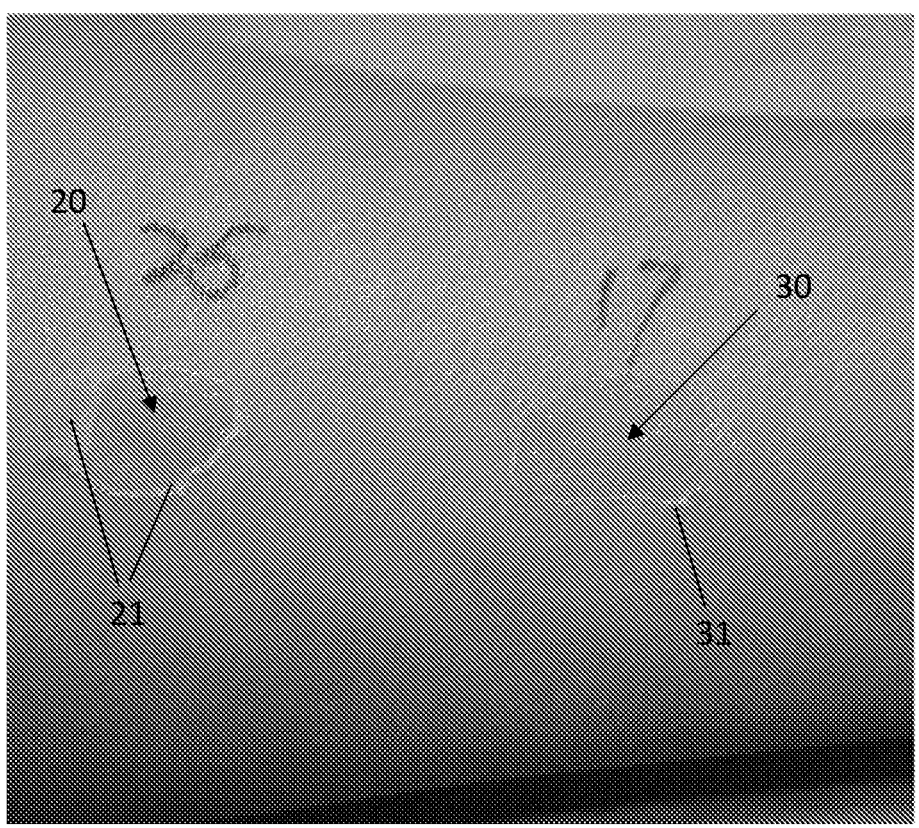
FIG. 9 is a picture of an exemplary thin film applied to human skin using two different solvents.

In FIG. 9, the first formulation 20 and the second formulation 30 are applied to human skin, and show physical changes after 24 hours. As shown, the thin film comprising the first formulation 20 having a first and second solvent evaporation rate of 353% shows severe edging 21 extending around the entire periphery of the thin film. In contrast, the thin film comprising the second formulation 30 having a first and second solvent evaporation rate of 121% shows minor edging 31. Notably, the edging 31 is much less than the edging 21, and the edging 31 does not extend around the entire periphery of the thin film.

FIG. 9 illustrates that adhesion and other mechanical properties of thin films are dictated by the combination of different components rather than only by the polymer composition of the thin film.

Embodiments

The following embodiments describe various alternative aspects and configurations of thin films described herein.

Embodiment 1. A method of forming a film on a substrate, the method comprising applying a polyisocyanate, a polyfunctional nucleophile, and a chain extender to the substrate.

Embodiment 2. The method of Embodiment 1, wherein the polyisocyanate and the polyfunctional nucleophile are first combined to form a pre-polymer, and the chain extender is subsequently combined with the formed pre-polymer.

Embodiment 3. The method of Embodiment 1, wherein a ratio of isocyanate groups of the polyisocyanate to a total of hydroxyl and amino groups of the polyfunctional nucleophile and chain extender is between 1.5:1 and 1:1.

Embodiment 4. The method of Embodiment 1, further comprising applying a solvent to the substrate.

Embodiment 5. The method of Embodiment 4, wherein the solvent is an antimicrobial solvent.

Embodiment 6. The method of Embodiment 5, wherein the antimicrobial solvent sterilizes a surface of the substrate.

Embodiment 7. The method of Embodiment 5, wherein the antimicrobial solvent comprises ethanol, propanol, isopropanol, butanol, isobutanol, or any combination thereof.

Embodiment 8. The method of Embodiment 4, wherein the solvent comprises water, acetone, ethanol, methyl ethyl ketone, ethanol, isopropanol, methyl acetate, ethyl acetate, butyl acetate, methyl propyl acetate, methyl isobutylketone, tetrahydrofuran, N-methylcyclohexanone, a siloxane, a linear alkane, a branched alkane, a cyclic alkane, or any combination thereof.

Embodiment 9. The method of Embodiment 8 wherein the siloxane comprises hexamethyldisiloxane, octamethyltrisiloxane, hexamethylcyclotrisiloxane or octamethylcyclotetrasiloxane.

Embodiment 10. The method of Embodiment 1, further comprising applying a first solvent and a second solvent to the substrate.

Embodiment 11. The method of Embodiment 10, wherein an evaporation rate of the first solvent and an evaporation rate of the second solvent are within 150% of each other, the percentage being based on the larger value; or within 50 to 1500% of the references n-butyl acetate (ER of n-butyl acetate is 100 mmHg*g/mol at 20° C.).

Embodiment The method of Embodiment 10, wherein a mixture of the first solvent and the second solvent has a polarity index of 1 to 7 or a dielectric constant of 2 to 30.

Embodiment 13. The method of Embodiment 10, wherein a mixture of the first solvent and the second solvent has a total vapor pressure of 4 to 70 mmHg according to Raoult's law.

Embodiment 14. The method of Embodiment 1, wherein the polyisocyanate is an aliphatic polyisocyanate.

Embodiment 15. The method of Embodiment 14, wherein the polyisocyanate comprises hexamethylene diisocyanate (HDI), isophorone diisocyanate (IPDI), bis(4-isocyanatocyclohexyl) methane, butane diisocyanate (BDI), a lysine diisocyanate, or any combination thereof.

Embodiment 16. The method of Embodiment 1, wherein the polyfunctional nucleophile is aliphatic and comprises a polyol, a polyamine, a mercaptan, or any combination thereof.

Embodiment 17. The method of Embodiment 16, wherein the polyfunctional nucleophile has a weight average molecular weight of 200-10,000.

Embodiment 18. The method of Embodiment 1, wherein the chain extender is an aliphatic, a siloxane or an ether.

Embodiment 19. The method of Embodiment 18, wherein the aliphatic, the siloxane, and the ether are a polyamine, a polyol, or any combination thereof.

Embodiment 20. The method of Embodiment 19, wherein the aliphatic polyamine comprises ethylene diamine, butylene diamine, pentylene diamine, hexamethylenediamine, isophorondiamine, a piperizine, or any combination thereof.

Embodiment 21. The method of Embodiment 19, wherein the ether comprises amine terminated polypropylene glycols, amine terminated polyethylene glycols, or any combination thereof.

Embodiment 22. The method of Embodiment 21, wherein the polyol is butanediol, propanediol, hexanediol, cyclohexane dimethanol, or any combination thereof.

Embodiment 23. The method of Embodiment 1, wherein the film is non-cytotoxic according to ISO 10993.

Embodiment 24. The method of Embodiment 1, wherein the film has implantation compatibility according to ISO 10993.

Embodiment 25. The method of Embodiment 1, wherein the film is non-pyrogenic according to ISO 10993.

Embodiment 26. The method of Embodiment 1, wherein the film is a non-irritant according to ISO 10993.

Embodiment 27. The method of Embodiment 1, wherein the film is non-sensitizing according to ISO 10993.

Embodiment 28. The method of Embodiment 1, wherein the film does not exhibit systemic toxicity according to ISO 10993.

Embodiment 29. The method of Embodiment 1, wherein the film forms a microbial barrier over the substrate.

Embodiment 30. The method of Embodiment 1 further comprising applying an additive to the substrate.

Embodiment 31. The method of Embodiment 30, wherein the additive comprises an antimicrobial agent, growth factors, peptides, therapeutic agents, biological regenerative agents, cosmetic agents, dyes, metal anti-oxidants, or any combination thereof.

Embodiment 32. A film forming composition, the composition comprising:
    an aliphatic polyisocyanate;
    an aliphatic polyfunctional nucleophile;
    an aliphatic chain extender; and
    a solvent.

Embodiment 33. A composition comprising a thin film, the thin film comprising a polymer formed from a reaction product of:
    an aliphatic polyisocyanate;
    an aliphatic polyfunctional nucleophile; and
    an aliphatic chain extender.

Embodiment 34. The composition of Embodiment 32 or Embodiment 33, wherein the polyisocyanate and the polyfunctional nucleophile are combinable to form a pre-polymer.

Embodiment 35. The composition of Embodiment 34, wherein the chain extender is combinable with the pre-polymer to form a final polymer solution.

Embodiment 36. The composition of Embodiment 32 or Embodiment 33, wherein a ratio of isocyanate groups of the polyisocyanate to a total of hydroxyl and amino groups of the polyfunctional nucleophile and chain extender is 1.5:1 to 1:1.

Embodiment 37. The composition of Embodiment 32, wherein the solvent is an antimicrobial solvent.

Embodiment 38. The composition of Embodiment 37, wherein the antimicrobial solvent comprises ethanol, propanol, isopropanol, butanol, or isobutanol.

Embodiment 39. The composition of Embodiment 32, wherein the solvent comprises a first solvent and a second solvent.

Embodiment 40. The composition of Embodiment 39, wherein an evaporation rate of the first solvent and an evaporation rate of the second solvent are within 150% of each other, the percentage being based on the larger value; or within 50 to 1500% of the references n-butyl acetate (ER of n-butyl acetate is 100 mmHg*g/mol at 20° C.).

Embodiment 41. The composition of Embodiment 39, wherein a mixture of the first solvent and the second solvent has a polarity index of 1 to 7 or a dielectric constant of 2 to 30.

Embodiment 42. The composition of Embodiment 39, wherein a mixture of the first solvent and the second solvent has a total vapor pressure of 4 to 70 mmHg according to Raoult's law.

Embodiment 43. The composition of Embodiment 32, wherein the solvent comprises water, acetone, ethanol, methyl ethyl ketone, ethanol, isopropanol, methyl acetate, ethyl acetate, butyl acetate, methyl propyl acetate, methyl isobutylketone, tetrahydrofuran, N-methylcyclohexanone, a siloxane, a linear alkane, a branched alkane, a cyclic alkane, or any combination thereof.

Embodiment 44. The composition of Embodiment 43, wherein the siloxane comprises hexamethyldisiloxane, octamethyltrisiloxane, hexamethylcyclotrisiloxane, octamethylcyclotetrasiloxane, or any combination thereof.

Embodiment 45. The composition of Embodiment 32 or Embodiment 33, wherein the polyisocyanate is an aliphatic polyisocyanate.

Embodiment 46. The composition of Embodiment 32 or Embodiment 33, wherein the polyisocyanate comprises hexamethylene diisocyanate (HDI), isophorone diisocyanate (IPDI), bis(4-isocyanatocyclohexyl) methane, butane diisocyanate (BDI), a lysine diisocyanate, or any combination thereof.

Embodiment 47. The composition of Embodiment 32 or Embodiment 33, wherein the polyfunctional nucleophile comprises a polyol, a polyamine, a mercaptan, or any combination thereof.

Embodiment 48. The composition of Embodiment 47, wherein the polyol has a weight average molecular weight of 200-10,000.

Embodiment 49. The composition of Embodiment 32 or Embodiment 33, wherein the chain extender is an aliphatic, a siloxane, or an ether.

Embodiment 50. The composition of Embodiment 49, wherein the aliphatic, siloxane, and ether are a polyamine, a polyol, or any combination thereof.

Embodiment 51. The composition of Embodiment 50, wherein the aliphatic polyamine comprises ethylene diamine, butylene diamine, pentylene diamine, hexamethylenediamine, isophorondiamine, a piperizine, or any combination thereof.

Embodiment 52. The composition of Embodiment 50, wherein the ether comprises an amine terminated polypropylene glycol, an amine terminated polyethylene glycol, or a combination of both.

Embodiment 53. The method of Embodiment 50, wherein the aliphatic polyol comprises butanediol, propanediol, hexanediol, cyclohexane dimethanol, or any combination thereof.

Embodiment 54. The composition of Embodiment 33, wherein the film has a strain rate of 100% to 1000%.

Embodiment 55. The composition of Embodiment 33, wherein the film has an average thickness of 20 to 250 microns.

Embodiment 56. The composition of Embodiment 33, wherein the film has a water vapor transmission rate of 300 to 600 g/m$^2$/day.

Embodiment 57. The composition of Embodiment 33, wherein the film has a Young's modulus of 6.0 to 10.0 MPa.

Embodiment 58. The composition of Embodiment 33, wherein the film has a tensile strength of 10 to 60 MPa.

Embodiment 59. The composition of Embodiment 33, wherein the film has a molecular weight of $1.0 \times 10^4$ g/mol to $5.0 \times 10^5$ g/mol.

Embodiment 60. The composition of Embodiment 33, wherein the film is non-cytotoxic according to ISO 10993.

Embodiment 61. The composition of Embodiment 33, wherein the film has implantation compatibility according to ISO 10993.

Embodiment 62. The composition of Embodiment 33, wherein the film is non-pyrogenic according to ISO 10993.

Embodiment 63. The composition of Embodiment 33, wherein the film is a non-irritant according to ISO 10993.

Embodiment 64. The composition of Embodiment 33, wherein the film is non-sensitizing according to ISO 10993.

Embodiment 65. The composition of Embodiment 33, wherein the film does not exhibit systemic toxicity according to ISO 10993.

Embodiment 66. The composition of Embodiment 33, wherein the thin film forms a microbial barrier when the thin film is disposed on a substrate surface.

Embodiment 67. The composition of Embodiment 32 or Embodiment 33, further comprising an additive.

Embodiment 68. The composition of Embodiment 67, wherein the additive comprises an antimicrobial agent, growth factors, peptides, therapeutic agents, biological regenerative agents, cosmetic agents, a metal anti-oxidant, or any combination thereof.

Embodiment 69. A method of protecting a metal surface from oxidation, the method comprising applying the composition of Embodiment 32 to the metal surface.

Embodiment 70. A method of coating a surface of biological tissue, the method comprising applying the composition of Embodiment 32 to the surface of the biological tissue.

The invention claimed is:
1. A film forming composition comprising:
an aliphatic polyisocyanate;
an aliphatic polyfunctional nucleophile;
a chain extender;
a first solvent; and
a second solvent different from the first solvent,
wherein an evaporation rate of the first solvent and an evaporation rate of the second solvent are within 150% of each other, the percentage being based on the larger value, wherein the evaporation rate of the first solvent and the evaporation rate of the second solvent are each calculated according to Equation 1:

Evaporation Rate=Vapor pressure*Molecular weight/11 the vapor pressure being measured at 20° C., and
wherein the first solvent and the second solvent selected from the group consisting of:
an alcohol and a ketone;
an alcohol and an acetate; or
an alcohol and an ester.

2. A method of coating a surface of biological tissue, the method comprising:
applying a composition to the surface of the biological tissue,
wherein the composition comprises:
an aliphatic polyisocyanate;
an aliphatic polyfunctional nucleophile;
a chain extender;
a first solvent; and
a second solvent different from the first solvent,
wherein an evaporation rate of the first solvent and an evaporation rate of the second solvent are within 150% of each other, the percentage being based on the larger value, and
wherein the evaporation rate of the first solvent and the evaporation rate of the second solvent are each calculated according to Equation 1:

Evaporation Rate=Vapor pressure*Molecular weight/11 the vapor pressure being measured at 20° C., and
wherein the first solvent and the second solvent selected from the group consisting of:
an alcohol and a ketone;
an alcohol and an acetate; or
an alcohol and an ester.

3. The method of claim 2, wherein the polyisocyanate and the polyfunctional nucleophile are combinable to form a pre-polymer.

4. The method of claim 3, wherein the chain extender is combinable with the pre-polymer to form a thin film-forming polymer solution.

5. The method of claim 2, wherein a ratio of isocyanate groups of the polyisocyanate to a total of hydroxyl and amino groups of the polyfunctional nucleophile and chain extender is 1.5:1 to 1:1.

6. The method of claim 2, wherein the first solvent, second solvent, or both are an antimicrobial solvent.

7. The method of claim 6, wherein the antimicrobial solvent comprises ethanol, propanol, isopropanol, butanol, isobutanol, or any combination thereof.

8. The method of claim 2, wherein the evaporation rate of the first solvent and the evaporation rate of the second solvent are within 50 to 1500% of an evaporation rate of n-butyl acetate.

9. The method of claim 2, wherein a mixture of the first solvent and the second solvent has a polarity index of 1 to 7 or a dielectric constant of 2 to 30.

10. The method of claim 2, wherein a mixture of the first solvent and the second solvent has a total vapor pressure of 4 to 70 mmHg according to Raoult's law.

11. The method of claim 2, wherein the first solvent and the second solvent comprise acetone, ethanol, methyl ethyl ketone, isopropanol, methyl acetate, ethyl acetate, butyl acetate, methyl propyl acetate, methyl isobutylketone, N-methylcyclohexanone, or any combination thereof.

12. The method of claim 2, wherein the polyisocyanate comprises hexamethylene diisocyanate (HDI), isophorone diisocyanate (IPDI), bis(4-isocyanatocyclohexyl) methane, butane diisocyanate (BDI), a lysine diisocyanate, lysine triisocyanate, tris(6-isocyanatohexyl) isocyanurate or any combination thereof.

13. The method of claim 2, wherein the aliphatic polyfunctional nucleophile comprises a polyol, a polyamine, a mercaptan, or any combination thereof.

14. The method of claim 2, wherein the chain extender is an aliphatic polyamine, a siloxane, or an ether.

15. The method of claim 13, wherein the aliphatic polyamine comprises ethylene diamine, butylene diamine, pentylene diamine, hexamethylenediamine, isophorondiamine, a piperizine, or any combination thereof.

16. The method of claim 2, wherein a film formed by the composition has an average thickness of 20 to 250 microns.

17. The method of claim 2, wherein the composition further comprises an additive, the additive comprising an antimicrobial agent, a growth factor, a peptide, a therapeutic agent, a biological regenerative agent, a cosmetic agent, a metal anti-oxidant, or any combination thereof.

18. A method of forming a film on a substrate, the method comprising:
combining a polyisocyanate with a polyol to form a polyurethane pre-polymer;
combining the polyurethane pre-polymer with a chain extender to form a polymer; and
applying the polymer to the substrate,
wherein the pre-polymer and/or the polymer are formed in a first solvent and a second solvent mixture,
wherein an evaporation rate of the first solvent and an evaporation rate of the second solvent are within 150% of each other, the percentage being based on the larger value; or within 50 to 1500% of the evaporation rate of n-butyl acetate, and
wherein the first solvent and the second solvent selected from the group consisting of:
an alcohol and a ketone;
an alcohol and an acetate; or
an alcohol and an ester.

19. The method of claim 18, wherein a mixture of the first solvent and the second solvent has a polarity index of 1 to 7 or a dielectric constant of 2 to 30.

20. The method of claim 18, wherein a mixture of the first solvent and the second solvent has a total vapor pressure of 4 to 70 mmHg according to Raoult's law.

21. The method of claim 18, wherein the first solvent and the second solvent comprise acetone, ethanol, methyl ethyl ketone, propanol, isopropanol, butanol, isobutanol, methyl acetate, ethyl acetate, butyl acetate, methyl propyl acetate, methyl isobutylketone, N-methylcyclohexanone, or any combination thereof,
wherein the first solvent is different from the second solvent.

22. The method of claim 18, wherein the first solvent and second solvent mixture is an antimicrobial solvent that sterilizes a surface of the substrate.

23. The method of claim 18, wherein the polyisocyanate is an aliphatic polyisocyanate.

24. The method of claim 23, wherein the polyisocyanate comprises hexamethylene diisocyanate (HDI), isophorone diisocyanate (IPDI), bis(4-isocyanatocyclohexyl) methane, butane diisocyanate (BDI), a lysine diisocyanate, lysine triisocyanate, tris(6-isocyanatohexyl) isocyanurate or any combination thereof.

25. The method of claim 18, wherein the chain extender comprises:
- an aliphatic polyamine including ethylene diamine, butylene diamine, pentylene diamine, hexamethylenediamine, isophorondiamine, piperizine, or any combination thereof;
- an ether including an amine terminated polypropylene glycol, an amine terminated polyethylene glycol, or a combination thereof; or
- a combination of the aliphatic polyamine and the ether.

* * * * *